United States Patent [19]

Kojima et al.

[11] 4,439,340
[45] Mar. 27, 1984

[54] CYANO-MONO-OR DIPHENYLBICYCLOHEXANE DERIVATIVES

[75] Inventors: Tetsuhiko Kojima; Masakazu Tsuji; Shigeru Sugimori, all of Kanagawaken, Japan

[73] Assignee: Chisso Corporation, Osaka, Japan

[21] Appl. No.: 396,484

[22] Filed: Jul. 8, 1982

[30] Foreign Application Priority Data

Jul. 9, 1981 [JP] Japan ............................ 56-107382
Aug. 18, 1981 [JP] Japan ............................ 56-129069

[51] Int. Cl.³ .................. C09K 3/34; C07C 121/60
[52] U.S. Cl. ........................ 252/299.63; 260/465 R
[58] Field of Search ............. 260/465 R; 252/299.63

[56] References Cited

U.S. PATENT DOCUMENTS 4,130,502  12/1978  Eidenschink et al. .............. 252/299

FOREIGN PATENT DOCUMENTS 2701591  7/1978  Fed. Rep. of Germany .

Primary Examiner—Dolph H. Torrence
Attorney, Agent, or Firm—Wenderoth, Lind & Ponack

[57] ABSTRACT

Liquid crystal compounds used for liquid crystal display elements are provided, which exhibit a liquid crystal phase within a broad temperature range and also have a low viscosity. The compounds are cyano-mono- or diphenylbicyclohexane derivatives expressed by the general formula

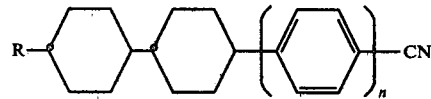

wherein R represents hydrogen or an alkyl group of 1 to 15 carbon atoms and n is 1 or 2.

4 Claims, No Drawings

CYANO-MONO-OR DIPHENYLBICYCLOHEXANE DERIVATIVES

BACKGROUND OF THE INVENTION

This invention relates to novel liquid crystal substances which exhibit a positive dielectric anisotropy.

Liquid crystal display elements utilize optical anisotropy and dielectric anisotropy of liquid crystal substances, and are classified into various types such as TN type, DS type, guest-host type, DAP type, White-Tailor type, etc. according to their display modes, and the properties of liquid crystal substances required for their respective uses are different. For example, liquid crystal substances having a positive dielectric anisotropy value Δε or those having a negative one may be required, or those having an intermediate value therebetween may be suitable, depending on the kind of the display elements. Liquid crystal substances should exhibit a liquid crystal phase within as broad a temperature range as possible and also be stable to moisture, heat, air, light, etc. At present, however, no single compound alone satisfies such conditions, and it is the present status that several kinds of liquid crystal compounds or non-liquid-crystal compounds have been blended together to obtain practically usable liquid crystal compositions.

Recently, liquid crystal display elements which are actuated within a broader temperature range than previous ones, i.e. within a temperature range from a lower temperature (about −20° C.) to a higher temperature (about 80° C.) have come to be required. Thus, as a constituent of liquid crystals applicable to the above-mentioned use, liquid crystal compounds which exhibit a liquid crystal phase within a broader temperature range and also have a lower viscosity have been needed.

An example of liquid crystal compounds used for such an object is compounds expressed by the general formula

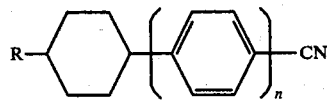

wherein R represents an alkyl group and n is 1 or 2. Among these compounds, cyanophenylalkylcyclohexanes (compounds where n=1 in the above formula) disclosed in U.S. Pat. No. 4,130,502 have a N-I point as low as about 50° C.; hence the above object cannot be fully attained. Further, cyanobiphenylalkylcyclohexanes (compounds where n=2 in the above formula) disclosed in Japanese patent application laid-open No. Sho 53-90251/1978 (West German patent application laid-open No. 2,701,591) have N-I points of about 220° C.; hence they are considerably useful for elevating liquid crystal temperature ranges, but have high viscosities of about 65 cp, which restricts the amount of such compounds which can be used. Thus, compounds which exhibit a nematic phase at higher temperatures and yet have a lower viscosity have been required. The object of the present invention is to provide compounds which satisfy such requirements.

SUMMARY OF THE INVENTION

The present invention is directed to cyano-mono- or diphenylbicyclohexane derivatives expressed by the general formula

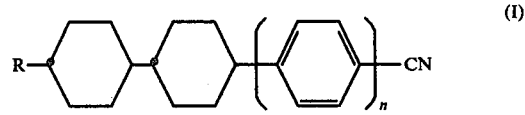

wherein R represents hydrogen atom or an alkyl group of 1 to 15 carbon atoms and n is 1 or 2.

The present invention is further directed to liquid crystal compositions containing the above compounds as well as liquid crystal display elements using such compositions.

DETAILED DESCRIPTION OF THE INVENTION

The compounds of the present invention have lower viscosities and yet broader liquid crystal temperature ranges. For example, 4-[trans-4′-(trans-4″-propylcyclohexyl)cyclohexyl]benzonitrile exhibits a liquid crystal phase within a temperature range as broad as crystalline-smectic point (C-Sm point): 73.6° C., smectic-nematic point (Sm-N point): 81.1° C. and nematic-transparent point (N-I point): 242.5° C. and its dielectric anisotropy and viscosity value are about +7 and about 58 cp at 20° C. (extrapolation value), respectively. Further, 4-cyano-4′-[trans-4″-trans-4‴-propylcyclohexylcyclohexyl]biphenyl exhibits a liquid crystal phase within a temperature range as broad as C-Sm point: 109.0, Sm-N point: 155.9° C. and N-I -point: 380° C. (extrapolation value) and its dielectric anisotropy value and viscosity are about +7 and about 80 cp at 20° C. (extrapolation value), respectively; it is stable to moisture, air, light, etc.; thus it is useful for preparing a nematic liquid crystal composition having a broader temperature range and also a lower viscosity when it is used in a small amount.

Next, a process for producing the compounds of the present invention will be described.

First, bromobenzene (in the case of n=1 in the above general formula (I)) or 4-bromobiphenyl (in the case of n=2 therein) is reacted with metallic magnesium to obtain 4-subsituted-mono- or biphenylmagnesium bromide ("mono- or biphenyl" will hereinafter be abbreviated merely to "phenyl"), which is then reacted with 4-(trans-4′-alkylcyclohexyl)cyclohexanone to obtain a 4-[4″-(trans-4‴-alkylcyclohexyl)cyclohexan-1″-ol]benzene derivative (II), which is then dehydrated in the presence of potassium hydrogen sulfate as catalyst to obtain a 4-[4″-(trans-4‴-alkylcyclohexyl)cyclohexen-1″-yl]benzene derivative (III), which is then hydrogenated in the presence of Raney nickel catalyst to obtain a 4-[trans-4″-(trans-4‴-alkylcyclohexyl)cyclohexyl]benzene derivative (IV). This compound can also be obtained even when the compound (II) is directly hydrogenated using Raney nickel catalyst. Next, the compound (IV) is halogenated with iodic acid, periodic acid or the like to obtain a 4-iodo-4′-[trans-4″-(trans-4‴-alkylcyclohexyl)cyclohexyl]benzene derivative (V), which is then cyanogenated with cuprous cyanide to give the objective cyanophenylbicyclohexane derivative. The above reactions are expressed by the following chemical formulas:

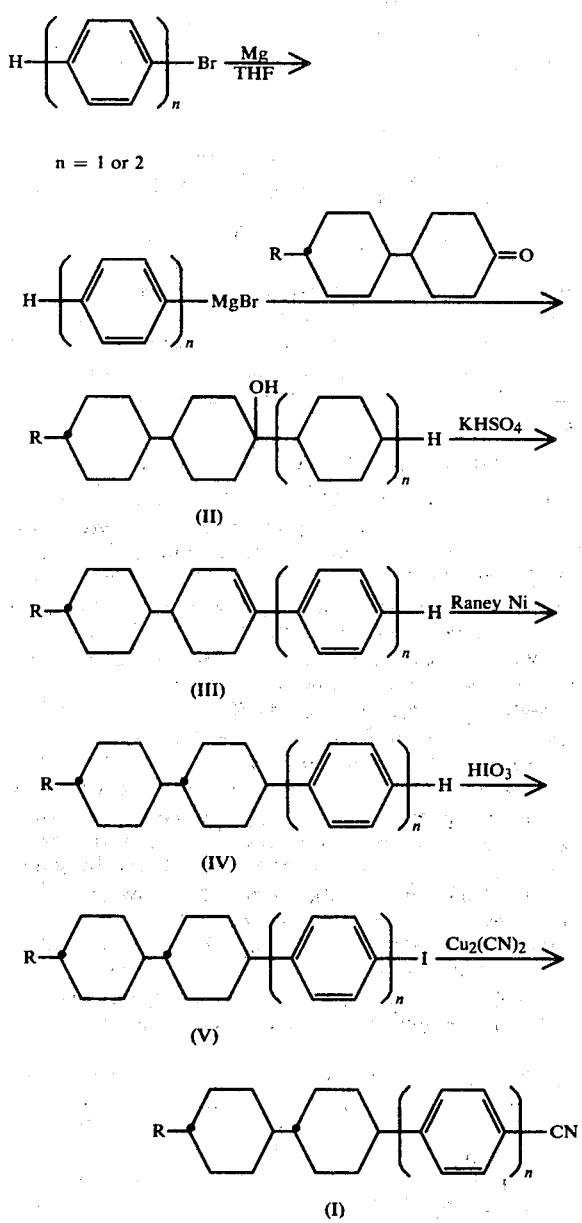

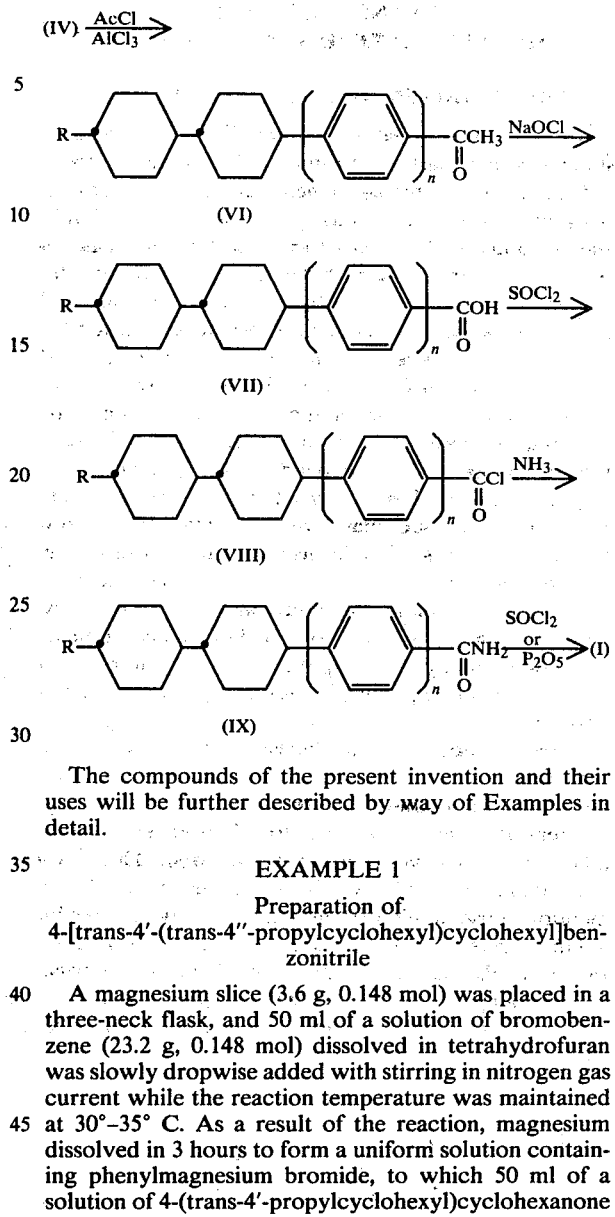

The compound of the formula (I) can also be prepared from the compound of the formula (IV) according to the following route although the number of steps is larger.

The compound of the formula (IV) is reacted with acetyl chloride or acetic anhydride in the presence of anhydrous aluminum chloride to obtain a 4-acetyl-4'-[trans-4''-(trans-4'''-alkylcyclohexyl)cyclohexyl]benzene derivative (VI), which is then subjected to haloform reaction with sodium hypobromite or sodium hypochlorite to convert the acetyl group into a carboxyl group to thereby obtain a carboxylic acid (VII), which is then converted with thionyl chloride into an acid chloride (VIII), which is, in turn, converted with ammonia into an acid amide (IX), which is then dehydrated with thionyl chloride or the like to obtain the compound of the formula (I). These reactions are expressed by the following formulas:

The compounds of the present invention and their uses will be further described by way of Examples in detail.

EXAMPLE 1

Preparation of 4-[trans-4'-(trans-4''-propylcyclohexyl)cyclohexyl]benzonitrile

A magnesium slice (3.6 g, 0.148 mol) was placed in a three-neck flask, and 50 ml of a solution of bromobenzene (23.2 g, 0.148 mol) dissolved in tetrahydrofuran was slowly dropwise added with stirring in nitrogen gas current while the reaction temperature was maintained at 30°–35° C. As a result of the reaction, magnesium dissolved in 3 hours to form a uniform solution containing phenylmagnesium bromide, to which 50 ml of a solution of 4-(trans-4'-propylcyclohexyl)cyclohexanone (26.2 g, 0.118 mol) dissolved in tetrahydrofuran was dropwise added as rapidly as possible while the reaction temperature was maintained at 10° C. or lower. After the dropwise addition, the mixture was heated up to 35° C. and agitated for 30 minutes, followed by adding 100 ml of 3 N hydrochloric acid. The reaction liquid was then taken into a separating funnel and subjected to extraction three times with n-heptane (100 ml), followed by washing the combined n-heptane layers with water until the wash water became neutral and then distilling off n-heptane under reduced pressure to give as an oily residue, [4'-(trans-4''-propylcyclohexyl)cyclohexan-1'-ol]benzene.

Potassium hydrogen sulfate (19 g) was added to the oily residue and the mixture was subjected to dehydration in nitrogen gas current at 170° C. for 2 hours. After cooling, n-heptane (200 ml) was added and potassium hydrogen sulfate was filtered off, followed by washing the resulting n-heptane layer with water until the wash water became neutral. n-Heptane was then distilled off under reduced pressure to give an oily substance as residue which was recrystallized from n-heptane and acetone to give objective [4'-(trans-4''-propylcyclohexyl)cyclohexene-1'-yl]benzene. This compound (7.5 g) was dissolved in ethanol (500 ml) and Raney nickel catalyst (3.2 g) was added, followed by catalytic reduction with hydrogen at 50° C. under atmospheric pressure. Both the raw material and the product were traced by gas chromatography. When the raw material disappeared, i.e. after 8 hours, the reduction reaction was completed. The quantity of hydrogen absorbed at that time was 800 ml. The catalyst was filtered off and the solvent was distilled off under reduced pressure. The resulting residue was recrystallized from ethanol to obtain [trans-4'-(trans-4''-propylcyclohexyl)cyclohexyl]benzene. This compound (1.4 g) was dissolved in acetic acid (50 ml), and purified water (0.9 ml), conc. sulfuric acid (1.0 ml), hydroiodic acid (0.20 g), iodine (0.50 g) and carbon tetrachloride (0.4 ml) were added, followed by subjecting the mixture to reflux at 80° C. for 5 hours. The reaction liquid was then cooled and the precipitated crystals were filtered, followed by recrystallizing the crystals from n-heptane to obtain 4-[trans-4'-(trans-4''-propylcyclohexyl)cyclohexyl]iodobenzene. This compound exhibited a liquid crystal state and had a C-Sm point of 119.0° C., a Sm-N point of 139.2° C. and a N-I point of 189.2° C. This compound (1.2 g) was dissolved in N,N-dimethylformamide (50 ml), and cuprous cyanide (0.63 g) was added, followed by reaction at 130° C. for 4 hours. n-Heptane (100 ml) was added and the liquid was transferred into a separating funnel, followed by separation with 30% aqueous ammonia, washing with water, washing with 6 N-hydrochloric acid and further washing with water until the wash liquid became neutral. The solvent was then distilled off and the resulting crystals were recrystallized from n-heptane to obtain objective 4-[trans-4'-(trans-4''-propylcyclohexyl)cyclohexyl]benzonitrile. Yield: 0.4 g (45% relative to the cyanogenation reaction). The compound had a C-Sm point of 73.1° C., a Sm-N point of 81.1° C. and a N-I point of 242.5° C.

The propyl group of the above 4-(trans-4'-propylcyclohexyl)cyclohexanone (0.118 mol) was replaced by H or pentyl to obtain 4-[trans-4'-(trans-cyclohexyl)cyclohexyl]benzonitrile or 4-[trans-4'-(trans-4''-pentylcyclohexyl)cyclohexyl]benzonitrile. The results are shown in Table 1.

(34.5 g, 0.148 mol) dissolved in tetrahydrofuran (100 ml) was slowly dropwise added with stirring in nitrogen gas current while the reaction temperature was maintained at 30°-35° C. After 3 hours, the reaction was complete, and magnesium dissolved to form a uniform solution containing 4-biphenylmagnesium bromide, to which a solution of 4-(trans-4'-propylcyclohexyl)cyclohexanone (26.2 g, 0.118 mol) dissolved in tetrahydrofuran (50 ml) was dropwise added as rapidly as possible while the reaction temperature was maintained at 10° C. or lower. After the dropwise addition, the mixture was heated up to 35° C. and agitated for 30 minutes, followed by adding 100 ml of 3 N hydrochloric acid. The reaction liquid was then taken into a separating funnel and subjected to extraction three times with n-heptane (each time, 100 ml), followed by washing the combined n-heptane layers with water until the wash water became neutral and then distilling off n-heptane under reduced pressure to give as a residue, 4-[4'-(trans-4'''-propylcyclohexyl)cyclohexan-1''-ol]biphenyl.

Potassium hydrogen sulfate (15 g) was added to the residue and the mixture was dehydrated in nitrogen gas current at 170° C. for 2 hours. After cooling, n-heptane (300 ml) was added and potassium hydrogen sulfate was filtered off, followed by washing the resulting n-heptane layer with water on a separating funnel until the wash water became neutral. n-Heptane was then distilled off under reduced pressure and the residue was recrystallized from n-heptane and acetone to give 4-[4''-(trans-4'''-propylcyclohexyl)cyclohexen-1''-yl]biphenyl. This compound (5.4 g, 0.0150 mol) was dissolved in ethanol (300 ml) and Raney nickel catalyst (2.2 g) was added, followed by catalytic reduction at 50° C. under a hydrogen pressure of 5 Kg/cm² in an autoclave. Both the raw material and the product were traced by gas chromatography. When the raw material disappeared, i.e. after 5 hours, the reduction reaction was completed. The quantity of hydrogen absorbed at that time was 410 ml. The catalyst was filtered off and the solvent was distilled off under reduced pressure. The resulting residue were recrystallized from n-heptane to obtain 4-[trans-4''-(trans-4'''-propylcyclohexyl)cyclohexyl]biphenyl. This compound (2.5 g, 0.0069 mol) was dissolved in acetic acid (200 ml), and purified water (1.3 ml), conc. sulfuric acid (1.4 ml), hydroiodic acid (0.28 g), iodine (0.71 g) and carbon tetrachloride (0.6 ml) were added, followed by subjecting the mixture to re-

TABLE 1

| In formula (I) | | Amount of raw material hexanone used | Yield | Yield* | Phase transition point (°C.) | | |
|---|---|---|---|---|---|---|---|
| n | R | (g) | (g) | (%) | C—Sm point or C—N point | Sm—N point | N—I point |
| 1 | H | 7.7 (0.0428 mol) | 0.4 | 44 | 94.6 | — | 61.0 (monotropic) |
| 1 | C₃H₇ | 26.2 (0.118 mol) | 0.4 | 45 | 73.6 | 81.1 | 238.9 |
| 1 | C₅H₁₁ | 29.5 (0.118 mol) | 0.6 | 56 | 53.8 | 60.3 | 234.4 |

*Yield at the cyanogenation step

EXAMPLE 2

Preparation of 4-cyano-4'-[trans-4''-(trans-4'''-propylcyclohexyl)cyclohexyl]biphenyl (compound of (R=C₂H₅) in the formula (I))

A magnesium slice (3.6 g, 0.148 mol) was placed in a three-neck flask, and a solution of 4-bromobiphenyl flux at 80° C. for 10 hours. The reaction liquid was then cooled and the precipitated crystals were filtered, followed by recrystallizing the crystals from n-heptane to obtain 4-iodo-4'-[trans-4''-(trans-4'''-propylcyclohexyl)cyclohexyl]biphenyl. This compound (2.1 g, 0.0043 mol) was dissolved in N,N-dimethylformamide (100 ml), and cuprous cyanide (0.77 g) was added, followed by reflux at 130° C. for 5 hours. After cooling, 30% aqueous ammonia (100 ml) was added to n-heptane (100 ml), followed by liquid separation, washing with water, washing with 6 N-hydrochloric acid and further washing with water until the wash liquid became neutral. The solvent was then distilled off and the resulting crystals were recrystallized from n-heptane to obtain 4-cyano-4'-[trans-4''-(trans-4'''-propylcyclohexyl)cyclohexyl]biphenyl. Yield: 0.7 g (42% relative to the cyanogenation reaction). The compound had a C-Sm point of 109.0° C., a Sm-N point of 155.9° C. and a N-I point of 380° C. (extrapolation value).

The propyl group of the above 4-(trans-4'-propylcyclohexyl)cyclohexanone was replaced by H or pentyl to obtain 4-cyano-4'-[trans-4''-(trans-4'''-alkylcyclohexyl)cyclohexyl]biphenyls. The results are shown in Table 2.

has a nematic temperature range of $-3°-+52°$ C. This liquid crystal composition was sealed in a TN cell (twisted nematic cell) having a cell thickness of 10 μm. The resulting material had an actuation threshold voltage of 1.53 V and a saturation voltage of 2.12 V. The composition had a viscosity of 23 cp at 20° C.

To the above liquid crystal composition (95 parts) was added 4-cyano-4'-[trans-4''-(trans-4'''-propylcyclohexyl)cyclohexyl]biphenyl (5 parts) of Example 2 of the present invention. The resulting liquid crystal composition had a broader temperature range of $-15°$ to $+64.0°$ C., and a material obtained by sealing this composition in the same TN cell as above (cell thickness: 10 μm) had an actuation threshold voltage of 1.63 V and a saturation voltage of 2.3 V. The viscosity of the composition was 25.6 cp at 20° C.

What is claimed is:

TABLE 2

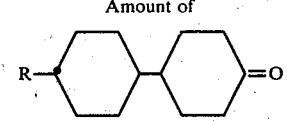

| In formula (I) | | Amount of used (g) | Yield (g) | Yield*¹ (%) | Phase transition point (°C.) | | |
|---|---|---|---|---|---|---|---|
| n | R | | | | C—Sm point | Sm—N point | N—I point |
| 2 | H | 21.3 (0.0118 mol) | 0.1 | 12 | 49.8 | 180.0 | 224.5 |
| 2 | C₃H₇ | 26.2 (0.0118 mol) | 0.7 | 42 | 109.0 | 155.9 | 380*² |
| 2 | C₅H₁₁ | 29.6 (0.0118 mol) | 0.5 | 53 | 63.8 | 132.7 | 360*² |

*¹Yield relative to the cyanogenation reaction
*²Extrapolation value

Next, use examples will be described. Parts referred to herein are by weight.

EXAMPLE 3

A liquid crystal composition (A) consisting of
trans-4-propyl-(4'-cyanophenyl)cyclohexane (24%),
trans-4-pentyl-(4'-cyanophenyl)cyclohexane (36%),
trans-4-heptyl-(4'-cyanophenyl)cyclohexane (25%), and
trans-4-pentyl-(4''-cyanobiphenyl)cyclohexane (15%)
has a nematic temperature range of $-10°-+72°$ C., a dielectric anisotropy value of +11, and a viscosity of 29 cp at 20° C.

In the above liquid crystal composition (A), trans-4-pentyl-(4''-cyanobiphenyl)cyclohexane was replaced by 4-[trans-4'-(trans-4''-pentylcyclohexyl)cyclohexyl]benzonitrile of Example 1 of the present invention in the same amount as that of the former compound. The resulting liquid crystal composition had a nematic temperature range of $-15°$ C. to $+75°$ C., a dielectric anisotropy value of +11 and a viscosity of 28 cp at 20° C. Thus the compounds of the present invention are optimal for broadening the nematic temperature range without elevating the viscosity.

EXAMPLE 4

A liquid crystal composition consisting of
trans-4-propyl-(4'-cyanophenyl)cyclohexane (28%),
trans-4-pentyl-(4'-cyanophenyl)cyclohexane (42%), and
trans-4-heptyl-(4'-cyanophenyl)cyclohexane (30%), 1. A compound expressed by the formula

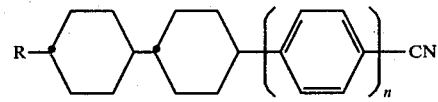

wherein R represents hydrogen or an alkyl group of 1 to 15 carbon atoms, and n is 1 or 2.

2. A compound expressed by the formula

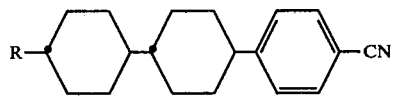

wherein R represents hydrogen or an alkyl group of 1 to 15 carbon atoms.

3. A compound expressed by the formula

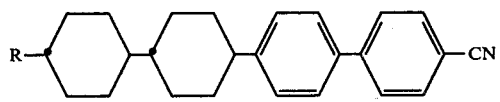

wherein R represents hydrogen or an alkyl group of 1 to 15 carbon atoms.

4. A liquid crystal composition which comprises a mixture of compounds at least one of which is a compound of claim 1.

* * * * *